United States Patent [19]

Kilgour

[11] Patent Number: 5,693,036
[45] Date of Patent: Dec. 2, 1997

[54] METHOD OF INJECTION MOULDING AN UNDERCUT FORMATION ON A CIRCULAR BODY AND A CLOSURE ASSEMBLY INCLUDING A COUPLING ELEMENT

[75] Inventor: Richard D. Kilgour, Reigate, United Kingdom

[73] Assignee: E. R. Squibb & Sons Inc., New York, N.Y.

[21] Appl. No.: 335,839

[22] PCT Filed: May 10, 1993

[86] PCT No.: PCT/GB93/00959

§ 371 Date: Nov. 30, 1994

§ 102(e) Date: Nov. 30, 1994

[87] PCT Pub. No.: WO93/23229

PCT Pub. Date: Nov. 25, 1993

[30] Foreign Application Priority Data

May 12, 1992 [GB] United Kingdom ............... 9210186
Nov. 5, 1992 [GB] United Kingdom ............... 9223225

[51] Int. Cl.⁶ ............... A61F 5/44; B65D 55/02; D01D 5/20
[52] U.S. Cl. ............... 604/338; 215/223; 215/201; 215/329; 206/536; 264/167
[58] Field of Search ............... 264/167; 215/201, 215/223, 317, 332, 329, 338–340; 604/332, 338, 342–344; 206/536, 807

[56] References Cited

U.S. PATENT DOCUMENTS

| | | |
|---|---|---|
| 3,339,546 | 9/1967 | Chen . |
| 3,782,574 | 1/1974 | Rumble . |
| 4,192,785 | 3/1980 | Chen et al. . |
| 4,257,526 | 3/1981 | Weits et al. ............... 215/332 |
| 4,320,230 | 3/1982 | Doyle . |
| 4,393,080 | 7/1983 | Pawelchak et al. . |
| 4,551,490 | 11/1985 | Doyle et al. . |

FOREIGN PATENT DOCUMENTS

| | | |
|---|---|---|
| B-75213/87 | 2/1988 | Australia . |
| B-15389/88 | 11/1988 | Australia . |
| B-45514/89 | 6/1990 | Australia . |
| B-75524/87 | 8/1990 | Australia . |
| 0 381 393 | 8/1990 | European Pat. Off. . |
| 2 103 410 | 4/1972 | France . |
| 2 385 386 | 10/1978 | France . |
| 26 38 619 | 3/1978 | Germany . |
| 31 10 201 | 9/1982 | Germany . |
| 1 571 657 | 7/1980 | United Kingdom . |
| 2 182 649 | 5/1987 | United Kingdom . |

Primary Examiner—Robert A. Clarke
Attorney, Agent, or Firm—Oliff & Berridge

[57] ABSTRACT

A method of injection moulding an undercut formation on a circular body in which the formation is moulded in a series of arcuate sections alternating with spaces. According to the method, the moulding core, which produces the formation, is extracted by firstly relatively rotating the body and the core so that the body is expanded radially and then ejecting the body off the core. The method is applicable to the manufacture of closure members and coupling elements.

29 Claims, 6 Drawing Sheets

METHOD OF INJECTION MOULDING AN UNDERCUT FORMATION ON A CIRCULAR BODY AND A CLOSURE ASSEMBLY INCLUDING A COUPLING ELEMENT

TECHNICAL FIELD

This invention relates to a method of moulding plastics articles, in particular to produce an article comprising an undercut formation on the inner surface of a cylinder, and to a novel plastics closure member and a novel plastics coupling element comprising such an undercut formation.

BACKGROUND ART

Moulding undercut formations, for example an internal flange around a circular lid or similar closure member, or around a ring coupling element, presents well known difficulties for injection moulding. The flange can be moulded by the use of an appropriately recessed core, but the radial extent of such a flange i.e. the amount of the undercut, must be relatively limited because of the need to extract the core from the moulding. Further, conventional techniques require the undercut to have a chamfered or sloped surface which can produce a camming action to stretch the moulding to get the flange past the mould core projection which formed it.

In moulding closure members and coupling elements from plastics materials, this need to have a chamfered or sloped surface can make the closure member or coupling element less secure and less positive, when for example, the closure member or coupling element is required to be a press fit over a lip on the external surface of a container or mating coupling element.

It has been proposed to produce undercut formations of the type described by injection moulding using a collapsing core, but in such cases the core leaves a so-called "witness line" on the moulded article, which is the imprint of the line between the movable parts of the collapsing core. In the case of a closure member or coupling element, this line can appear on the internal wall above the undercut and can severely limit the effectiveness of the seal made by the closure member or coupling element.

The invention aims to allow deeper undercuts which moreover do not need to be sloped, and to avoid the production of witness lines. A further object of the invention is to produce a novel closure member and a novel coupling element having a deeper undercut and a more secure closure and/or sealing action.

DISCLOSURE OF INVENTION

According to one aspect the present invention provides a method of injection moulding an undercut formation on a circular body, wherein said formation is moulded in a series of arcuate sections alternating with spaces, and wherein the moulding core which produces the formation is extracted by firstly relatively rotating said body and said core so that the body is expanded radially and then ejecting the body off the core.

The invention thus provides a method for forming moulded plastics article, and in particular a closure member or a coupling element, comprising an undercut formation on a circular body, said formation comprising a series of arcuate sections alternating with spaces, a plurality of the arcuate sections each having an undercut radially extending surface which subtends an angle to the axis of the body sufficient, in the case of a closure member or coupling element, to give a required degree of security to the article.

Certain closure members and coupling elements according to the invention are novel articles and are accordingly included within the invention.

Thus in a further aspect the invention provides a moulded plastics closure member comprising a circular body provided with an undercut formation, said formation comprising a series of arcuate sections alternating with spaces, ends of the respective arcuate sections being chamfered, the chamfered end surfaces of the arcuate sections being located at an angle of less than 60° to a tangent to the circular body, and a plurality of the arcuate sections each having an undercut radially extending surface which is disposed at an angle to the rotational axis of the body sufficient to give a required degree of security to the closure member.

In this aspect of the invention the moulded plastics closure member preferably comprises a circular body having an undercut formation and a seal on an internal wall above the undercut formation, said formation having a radial extent of greater than 0.005 inch (0.0125 cm) and comprising a series of arcuate sections alternating with spaces, a plurality of the arcuate sections each having an undercut radially extending surface which subtends an angle to the axis of the body of at least 80° and sufficient to give a required degree of security to the closure member, the internal wall above the undercut formation being devoid of witness lines (as hereinbefore defined).

In a still further aspect, the invention also provides a coupling element, and in particular a coupling element for use in an ostomy, incontinence, or wound care device, the element comprising an annular body provided with an undercut formation, said formation comprising a series of arcuate sections alternating with spaces, a plurality of the undercut arcuate sections each having a radially extending surface which is disposed at an angle to the rotational axis of the body sufficient to give a required degree of security to the coupling element.

The undercut formation is discontinuous in a peripheral direction, but its radial extent can be greater than that achievable by conventional moulding techniques, and its radially extending surface can be at a steeper angle to the axis of the body. The security of such a formation as a means of engagement can be much greater than that of previously known closure members and coupling elements.

The arcuate sections of the undercut formation can be of equal or unequal length, depending upon the application. Usually they will be of equal length, but it is envisaged that, for example, a child resist closure member may have a series of arcuate sections of unequal length which cooperate with discontinuities in a lip of a container such that, in order to open the container, the closure member needs to be rotated relative to the container until the arcuate sections are in register with the appropriate discontinuities of the lip. This position can, for example, be indicated by aligning arrows on the closure member and the container respectively.

Preferably the arcuate sections occupy as much of the periphery as possible, although for practical reasons, and in order to facilitate removal of the body from the core, preferably the ratio of the aggregate circumferential length of the spaces to the aggregate circumferential length of the arcuate sections is at least 1:3.

The spaces themselves can be of equal or unequal length, depending upon the application.

The radial extent of the undercut formation will depend on the application, and to an extent on the wall thickness of the body and the type of plastics material employed. However a radial extent of greater than 0.005 inch (0.0125 cm), and up to 0.020 inch (0.051 cm) or even more, can be achieved using the method of the invention in appropriate circumstances.

The radial extent of the undercut formation and the thickness and material of the body need to be such as to permit relative rotation of the core and the body. This relative rotation causes the body to expand radially as the arcuate sections ride up on the core. To facilitate this relative rotation, the respective arcuate sections are chamfered and the chamfered end surfaces of the arcuate sections are not radially directed, but are located at an acute angle to a tangent to the circular body. Preferably the angle is less than 60°, most preferably less than 45°.

The body can, if desired be rotated with respect to the core, however usually, the body will be held stationary and the core rotated by an amount sufficient to cause the arcuate sections to ride up out of the depressions in which they have been formed. The body can then easily be ejected from the core by any convenient means.

In the closure member and coupling element of the invention preferably each of the undercut arcuate sections has a radially extending surface which subtends an angle to the axis of the body sufficient to give the required degree of security thereto. This angle will usually be at least 70°, preferably 80°, and most preferably 90°. In some circumstances the angle may even exceed 90°, and extend to 95° or more, giving a slope opposite to that necessary using conventional moulding techniques.

By the use of a steep angle of slope it is found that, in many applications, when the closure member or coupling element is applied over a cooperating lip in a closure assembly, or on a mating coupling element, an audible click can be heard, which provides the user with reassurance that the closure member or coupling element is secure. It is also found that the greater the angle of slope the greater the security of mating to an external lip or flange on a container, or on a mating coupling element, particularly when that lip or flange has a radially extending surface which also subtends a steep angle to the axis of the body. 90° angle external lips and flanges are readily obtainable by injection moulding, and thus the invention provides for the first time the opportunity to obtain a closure or coupling assembly in which both the undercut formation on the closure member or coupling element and the lip on the component to which it is mated subtend a right angle to the axis of the closure assembly or coupling assembly without the presence of a witness line on an internal wall above the undercut formation.

The closure member of the invention may find application in a wide variety of products where it is necessary to form an effective seal between two mating parts. It is particularly useful in those circumstances in which the undercut formation is required on a relatively small circular body, and in those closure members in which the undercut formation is on the inside of an annular ring member of U-shaped cross-section.

Thus, for example, the invention may be applied to a closure member for child-resist containers, rendering the closure member more difficult to remove from the container as previously described. Improved security food containers represent a further application.

Containers to which the closure members of the present invention may be applied are disclosed in U.S. Pat. Nos. 3,860,133, 4,434,903, 3,782,574, and 3,871,662, UK Patent Application No. GB 2096108A and French Patent No. 2600977, and the entire disclosures of all these patents are incorporated herein by reference. It will be appreciated that hitherto in each case the manufacture of the embodiments disclosed in these patents will have been subject to the limitations and deficiencies of the prior art hereinbefore referred to.

This invention can also be embodied in a coupling element of an ostomy coupling. Such couplings are used to attach a bag for receiving discharged material to a medical grade adhesive pad which is attached to the wearer's peristomal skin surface.

Efforts have been made over the years to design an ostomy coupling which remains securely attached when coupled but which can be separated without causing pain to the peristomal region which is of course very tender in the days and weeks immediately following the surgical intervention procedure.

A successful design of ostomy coupling is described and claimed in British Patent No. 1571657 the entire disclosure of which is also incorporated herein by reference. This includes a channel-section coupling element which co-operates with a second coupling element carrying a rib of closed-loop form which is designed to inter-engage with the channel of the first coupling element, so that a snap-fit is achieved between the two coupling elements. The channel section element is preferably attached to the bag but may be attached instead to the medical grade adhesive pad. The second element is preferably attached to the pad but may be attached to the bag.

It has been found that better results are obtained, in terms of security of attachment of the two coupling elements, if certain ostensibly minor but in fact important new features are included in the coupling device described above. Such features include the provision of an undercut formation comprising a series of arcuate sections alternating with spaces in accordance with the invention, as previously described.

According to a still further aspect of the present invention, there is provided a ring-like coupling element of an ostomy coupling having a channel shape in cross section, defined by radially inner and outer walls and a floor, the element being characterised in that (i) the floor of the element has a plurality of depressions therein adjacent to the inner wall, the depressions being spaced around the channel, and (ii) the radially outer wall has a plurality of inwardly-projecting shelf-like roof portions, also spaced around the channel and extending partly across the channel from that part of the outer wall furthest from the channel floor.

With this arrangement, the security of attachment of the two coupling parts is enhanced by the overlap of the roof portions and the other coupling element; that is to say, the overlap of the roof portions tends to prevent the second (e.g. bag side) coupling element moving out of the channel in the axial direction of the coupling. Also, as will be understood from the above, the manufacture of the body side coupling element using injection moulding techniques is facilitated. It will be realised that the present invention provides the possibility for the use of more flexible side walls for the coupling element, enabling a lower application force to be used whilst providing a high degree of security by the use of an undercut formation with a steep angle of slope relative to the axis of the ostomy coupling element.

The invention may be applied to a wide range of plastics materials, including for example, olefin polymers and co-polymers such as polyethylene, polypropylene, and ethylene co-polymers such as ethylene-vinyl acetate co-polymers.

BRIEF DESCRIPTION OF DRAWINGS

In order that the invention may be clearly understood, exemplary embodiments thereof will now be described with reference to the accompanying Drawings, in which:

FIG. 3c shows an enlarged view of the circled area in FIG. 3a;

DETAILED DESCRIPTION OF DRAWINGS

Figure 1:
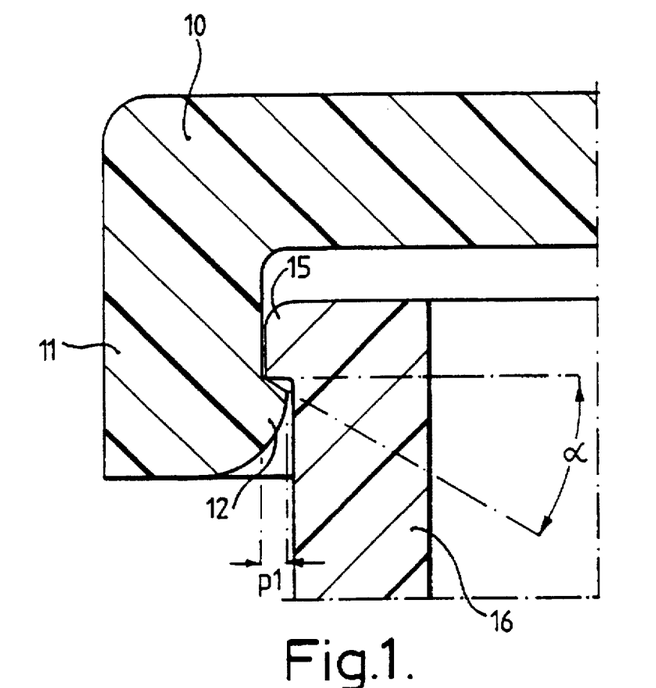
FIG. 1 shows a scrap sectional view of the design of a conventional undercut lid.

FIG. 1 shows one edge 11 of a circular lid member 10 in section with an inwardly turned flange 12 on the edge 11. The flange 12 projects by an amount p1 and its top surface slopes downwardly at an angle a. The lid mates with an outturned flange 15 on a cylindrical body 16. Flange 15 projects at right angles to the axis of the body 16.

In injection moulding the body 16, the production of flange 15 gives no problem because the outer parts of the mould can be separate and move apart to release the moulded article. This is not possible with the internal core required to produce the flange 12 on lid member 10. In that case, the core must be forcibly pulled out and the edge 11 and flange 12 must stretch to allow this. Thus, the distance p1 is restricted and the angle ∝ is a necessity in order that a camming action will occur between the mould core and the moulded article to stretch the article. It is apparent that lid 10 is not particularly secure on body 16, since a simple pull will separate the two.

Figure 2:
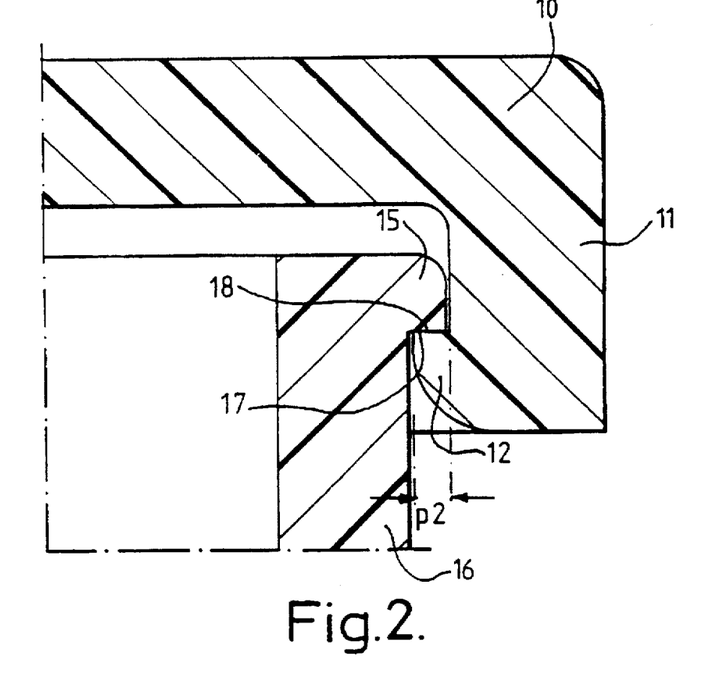
FIG. 2 similarly shows a possible new design of closure member using the method of the invention.

FIG. 2 shows a similar view of a moulded lid which can be produced by the method according to the invention. Distance p2 can be greater, and ∝ can be 0° or even a negative figure. With such a lid, the engagement of the two parts is much more secure since the mating surfaces 17, 18 of the flanges 12 and 15 will not allow them to separate easily.

Figure 3A:
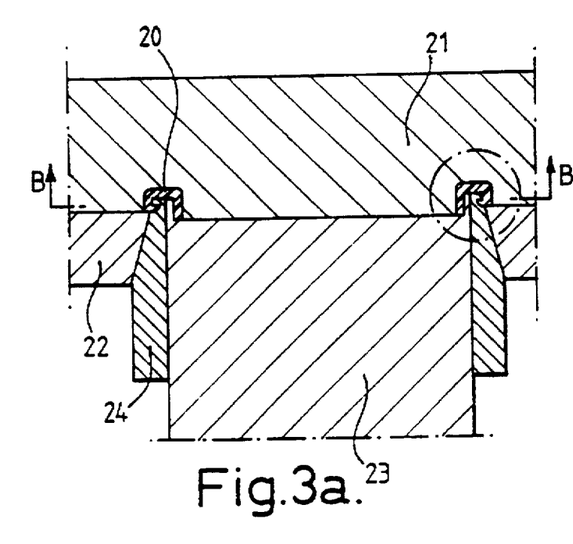
FIG. 3a is a sectional view of a first state in the moulding release procedure according to the invention taken along line A—A in FIG. 3b.
Figure 3B:
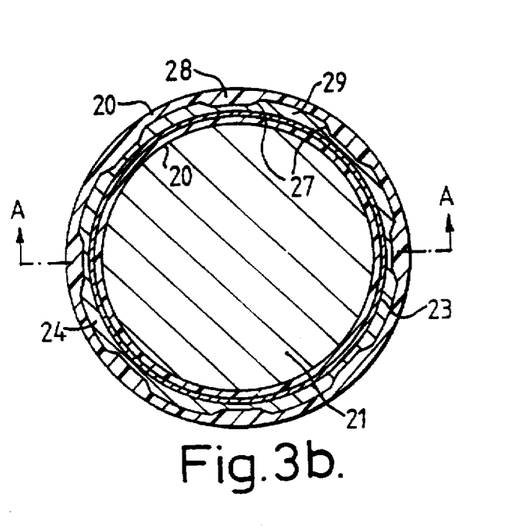
FIG. 3b is a cross section of the mould parts in the first stage.
Figure 3C:
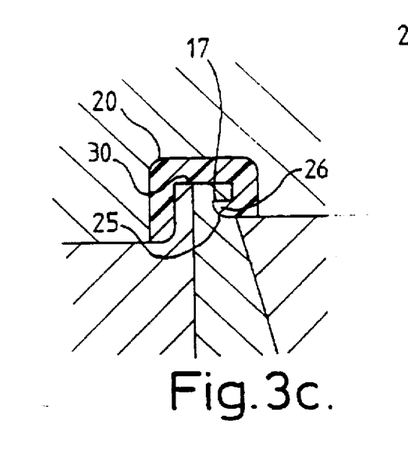
Figure 4A:
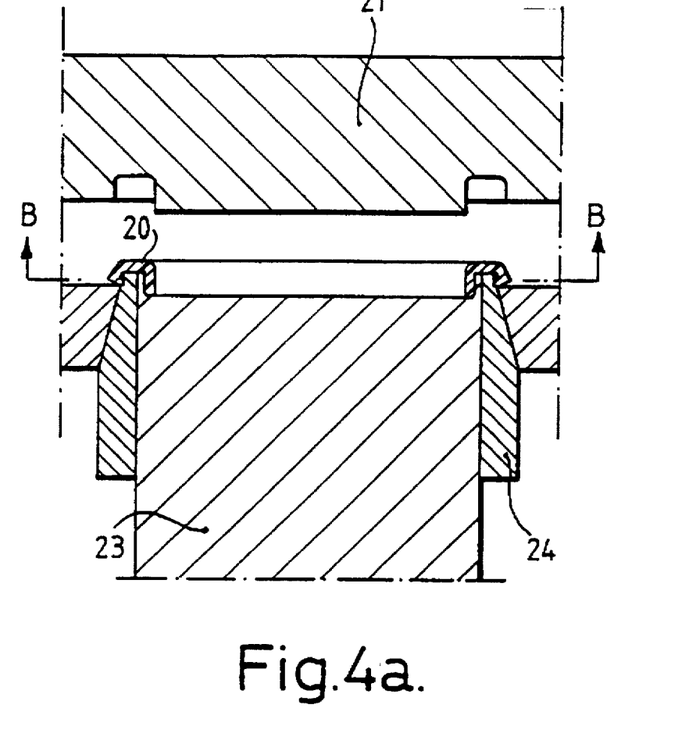
FIG. 4a is a sectional view of a second stage in the moulding release procedure according to the invention taken along line A—A in FIG. 4b.
Figure 4B:
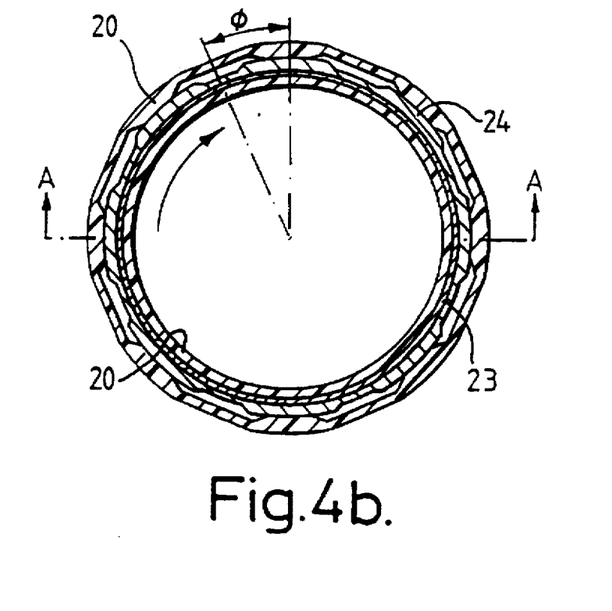
FIG. 4b is a cross section of the mould parts in the second stage.
Figure 5A:
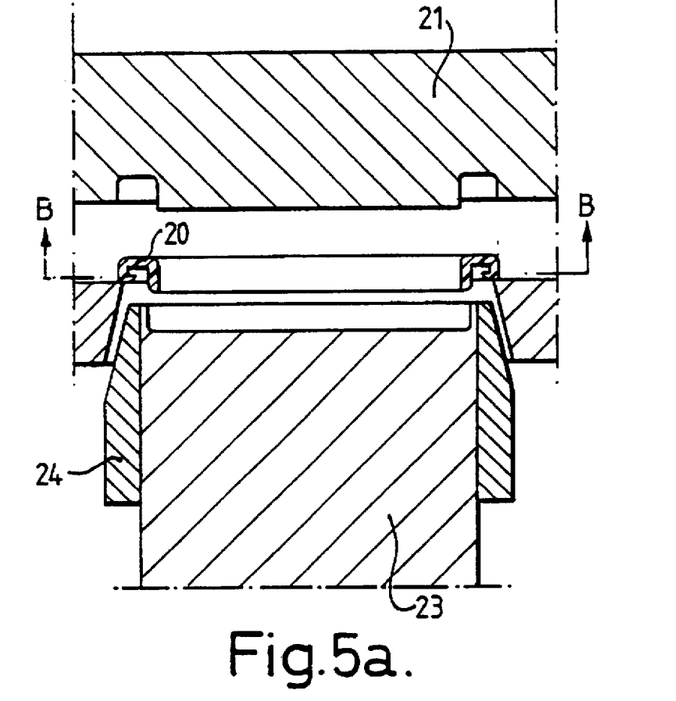
FIG. 5a is a sectional view of a third stage in the moulding release procedure according to the invention taken along line A—A in FIG. 5b.
Figure 5B:
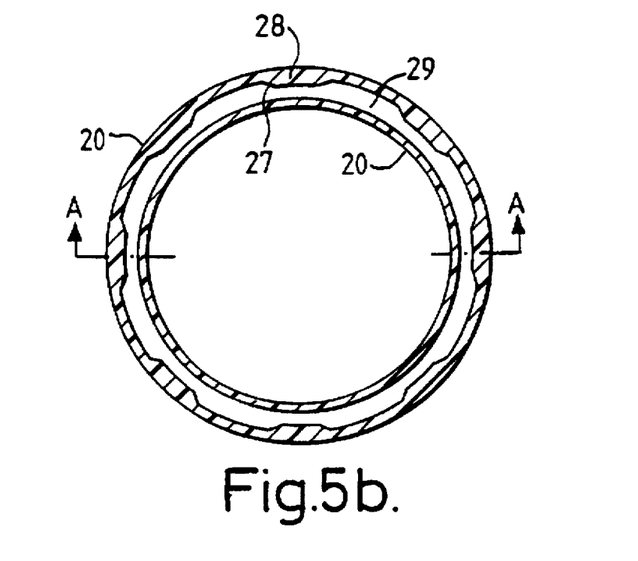
FIG. 5b is a cross section of the mould parts in the third stage.

The moulding technique is illustrated in FIGS. 3, 4 and 5 which show three stages in the release of the moulded part, in this case an undercut ring member 20. Four mould parts are required: a cavity member 21, a stripper member 22, an inner core member 23 and an outer core member 24. The latter is the one which includes the altered mould shape which defines the novel undercut flange.

FIG. 3a shows the stage when injection of moulding material has been completed and the article is ready for ejection. The shape of the outer core member 24 is seen clearly from FIGS. 3b and 3c. The groove 25 which forms the undercut flange 26 is discontinuous circumferentially. Thus, flange 26 is also discontinuous, but its surface 17 is not sloped. The ends 27 of the arcuate sections 28 and of the intervening spaces 29 of the flange 26 are however not radial but chamfered, as defined by the respective sections of groove 25. The sections 28 and the spaces 29 are of equal length.

In order to extract the moulded ring member 20, the cavity member 21 is first withdrawn (FIG. 4a). Then, the outer core member 24 is rotated (FIG. 4b) by the amount ∅ of one arcuate section 28. The chamfered ends 27 cam outwards against the ends of the groove 25 and the flange sections 28 ride up out of the groove (FIG. 4b). The ring 20 is then stretched outwards (FIG. 4a).

In this position, the inner and outer core member 23 and 24 can be withdrawn downwardly, or the stripper member 22 can move upwardly, to release the moulding (FIG. 5a), which figure also illustrates the ring 20 returned to its undistorted state.

The resultant lid or collar can have a greater degree of security when fitted to a mating member and is devoid of witness lines on the internal sealing wall 30.

It is found that because of the greater security obtained using undercut flanges having greater radial extent and steeper angle of slope with respect to the axis of the closure member, that the lid, collar or other closure member can be made from a softer or thinner material making it easier to press fit the closure member to a mating member such as a lipped ring or cylinder to form a closure assembly. Notwithstanding the improved ease of assembly, a high degree of security is maintained.

Referring now to FIGS. 6–11, these disclose the application of the invention to an ostomy coupling. It will normally be the case that the coupling element shown in FIG. 6 will be the bag-side element and that shown in FIG. 10 will be the body side element, but these elements may be reversed, that is, the FIG. 6 element may be the body side and the FIG. 10 element the bag-side, without departing from the invention.

Mutually inter-engagable coupling elements designed according to the principles illustrated in FIG. 6–11 may also be used as coupling elements in incontinence devices and in wound care appliances. As will be well understood by those skilled in the ostomy art, a relatively thin pad of medical grade adhesive material is normally attached at one of its surfaces to the skin of the wearer and at the other of its surfaces to the surface 163 shown in FIG. 10. Such a pad may have a stomal orifice therein or may have provision whereby its central portion can be pushed out or detached, so that waste material being discharged from the body of the wearer can pass into an ostomy bag or an incontinence device which is connected by the bag side coupling element 110 to the body side coupling element 160. Suitable materials for such an adhesive pad include, for example, those described by Chen in U.S. Pat. No. 3,339,546; by Chen et al in U.S. Pat. No. 4,192,785; by Pawelchak et al in U.S. Pat. No. 4,393,080; and by Doyle et al in U.S. Pat. No. 4,551,490, the entire disclosures of each of which are included herein by reference. A particularly suitable material is that sold under the Registered Trade Mark STOMAHESIVE by Bristol-Myers Squibb of Ickenham, Middlesex, England.

Referring firstly to FIGS. 6–9, one example of a bag side coupling element according to the invention is illustrated. It comprises a channel section element 110 of circular form seen in FIG. 6. The female ostomy coupling element may be normally made of a synthetic plastics material such as EVA. EVA Grade UL 00209 is one material, available from Esso, which is suitable. The male element may be made of low density polyethylene.

Figure 6:
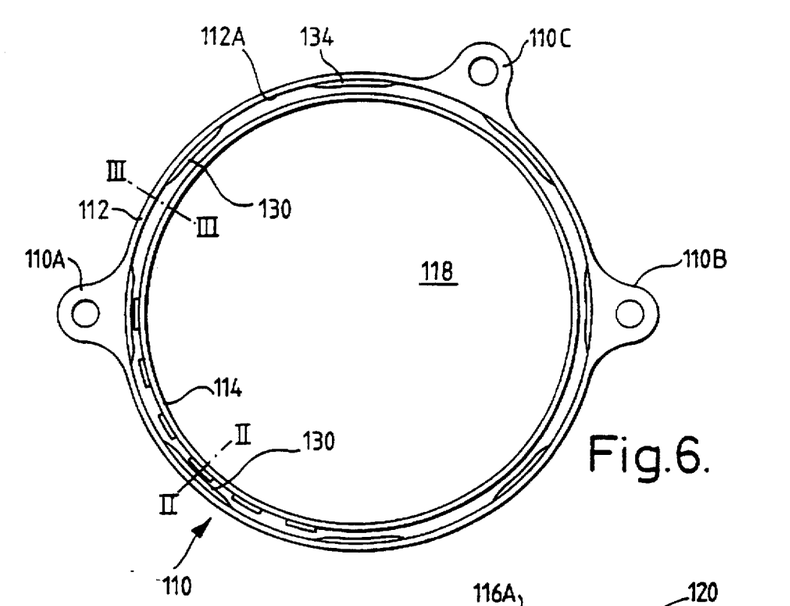
FIG. 6 is a plan view of one example of ostomy coupling element according to the invention.

The element 110 as seen in FIG. 6 has tabs 110A, 110B and 110C. The tabs 110A and 110B are provided to facilitate attachment of a belt, and the tab 110C is provided to afford a grasping point whereby the wearer may separate the two coupling elements by "peeling" them apart. The coupling element 110 has a radially outer wall 112 and a radially inner wall 114. The wall 114 surrounds a stomal orifice 118 at the centre of the coupling. The generally ring-like or annular element 110 has a floor 116 which joins the radially inner and outer walls 112, 114, this floor having a surface 116A to which may be attached, e.g. by adhesive, heat welding, RF plastics welding, or other suitable method, an ostomy bag provided with a suitable hole in one of its walls to serve as an entry for discharges from the wearer. This entry hole is aligned with the stomal orifice 118 as is conventional in ostomy bags. The floor 116 has a surface 116B at the base of the channel, and, into this floor, there are provided a plurality of recesses 120. These recesses 120 in their presently preferred form are relatively shallow, flat bottomed, and are equally spaced peripherally around the coupling element. As seen best in FIG. 8, the recesses 120 have a shape which is approximately rectangular. The recesses, however, could be differently shaped according to the design of the moulding equipment, if desired. In a preferred embodiment of the invention, there are 24 such recesses, spaced around the ring at 15° centres. The depth of each such recess is approximately 0.01 inch, i.e. approximately 0.254 millimetres. The remainder of the surface 116B at the base of the channel is substantially flat.

The recesses serve to receive one or more mould core members, for example inner core member 23 in FIGS. 3a–5a, and serve, in extraction of the annular body from the mould, to prevent rotation of said body relative to the said mould core member.

Figure 7:
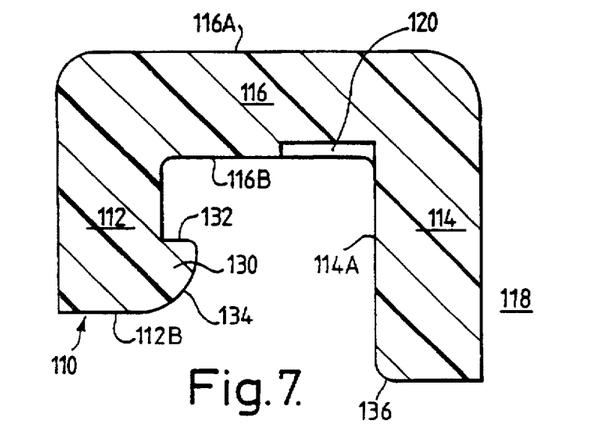
FIG. 7 is a cross-section in a radial plane on the line II—II in FIG. 6.
Figure 8:
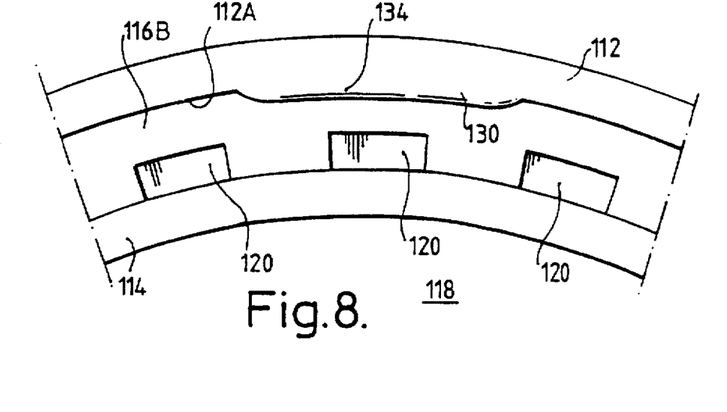
FIG. 8 is a plan view, on an enlarged scale compared to FIG. 6, of part of the element shown in FIG. 6.
Figure 9:
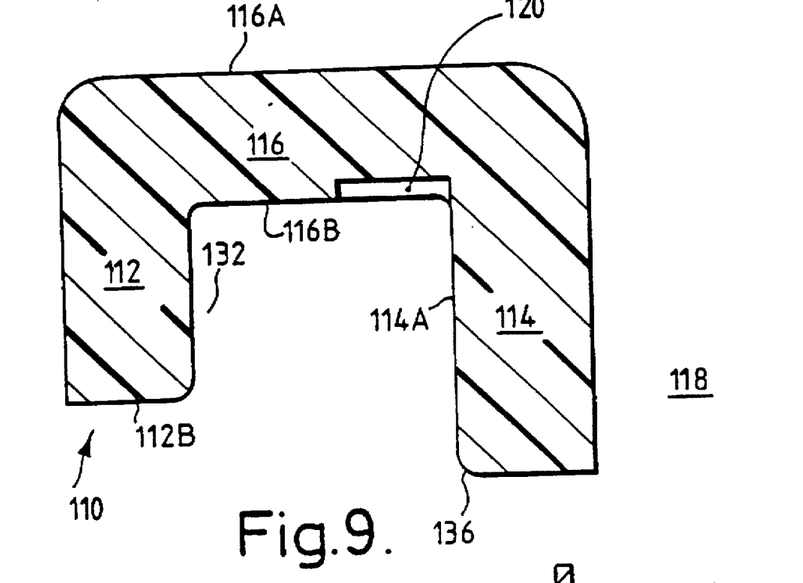
FIG. 9 is a cross-section similar to FIG. 7, but taken on the line III—III of FIG. 6.

The radially outer wall 112 is provided with a plurality of radially inwardly projecting roof-like portions 130 (also referred to herein as arcuate sections) whose undersides 132 (i.e. top surfaces as seen in FIG. 7, which are undersides of the portions 130 when the female coupling element is laid flat on a horizontal surface) are substantially flat and extend substantially in a plane parallel to the planes of the respective surfaces 116A and 116B. The portion 130 extends inwardly a distance such that it covers from about 10 to about 20%, and preferably about 15%, of the width of the channel as will be discussed later. In moulding terms, the portions 130 define undercut formations. The roof-like portions 130 may have radially inner surfaces defined by respective continuous curves 134 that extend from the end 112B of the wall 112 in a smooth curve to merge with the surface 132. In a peripheral sense, as seen in FIGS. 6 and 8 the walls 134 curve smoothly to merge with the radially inner surface 112A of the wall 112. This structure is provided so that the portions 130 are forced outwardly by rotation of the core, as described above, so permitting the coupling element to be readily removed from the mould.

The radially inner wall 114 is, as seen in FIG. 7, of greater height than the wall 112, and has its radially outer corner radiused as seen at 136. In combination, the surfaces 134 and 136 contribute to the ease with which a counterpart coupling element such as is seen in FIG. 10 can be pushed into an inter-engaged condition, relative to the coupling element 110.

The respective roof portions 130 are equally spaced around the inner periphery of the wall 112, and are preferably located at 45° centres. Other spacings, however, may be used. The extent in a peripheral sense of each roof portion 130 is such that it occupies an arc subtending at the axis of revolution of the coupling element, i.e. at the centre in the case of a geometrically circular ostomy coupling element, an angle of between 15° and 25°, preferably between about 18° and 22°. The number, positioning, and angular extent of the roof portions 130 may be varied. Preferably there are 6, 8, 10 or 12 of the roof portions, and the roof portions are preferably equally angularly spaced in a peripheral sense around the coupling element. The roof portions 130 may extend inwardly of the wall 112 by an amount of up to half the width of the channel, although preferably they extend by an amount equal to about one tenth to one fifth, more preferably one seventh to one fifth, and, most preferably one sixth, of the width of the channel measured in a radial direction. It has been found that this preferred amount of inward extent, taken together with the positioning, number and arrangement of the roof portions, gives an ostomy coupling having a sufficient overlap of the cooperating coupling elements that the security of attachment of the two coupling elements against a direct pull is enhanced, but the ease of separation of the two coupling elements by the "peeling method" referred to above is such that the separation can be readily achieved by most ostomy coupling wearers, except possibly those who are very old and infirm.

Figures 10, 11:
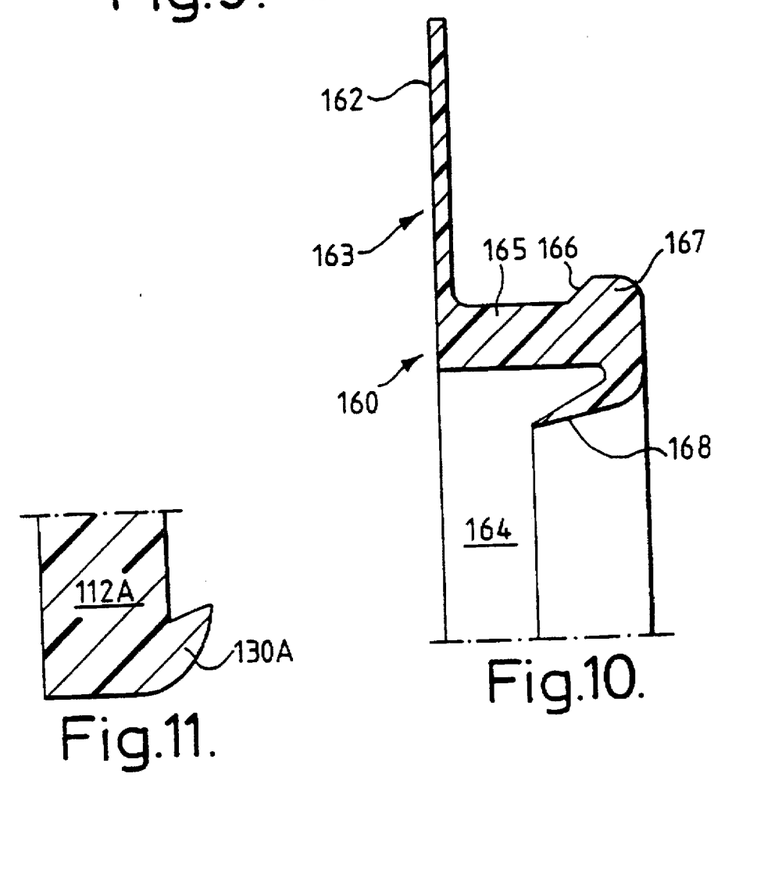
FIG. 10 is a cross-sectional view, the section being on a radial plane containing the longitudinal central axis of the coupling, and showing an ostomy coupling element which is a counterpart to the element shown in FIG. 6.
FIG. 11 is a detail view of part of the element shown in FIG. 6, illustrating an alternative shape for the undercut portion.

FIG. 10 illustrates, in partial cross-section, an ostomy coupling element 160, which is also of ring-like or annular form and intended to interfit with the element 110. In the preferred embodiment of the present invention, the element 160 would be the body side coupling element. It comprises a radially extending substantially flat flange 162 and a peripherally extending rib member 165 formed for mutual inter-engagement with coupling element 110. The flange 162 has a surface 163 to which is secured, in any suitable manner, a pad (not shown) of medical grade adhesive material.

As is conventional in ostomy couplings, provision may be made on the free surface of the medical grade adhesive pad for markings directed to assisting the user to cut out a central portion of the pad, in registry with the stomal orifice 164. The rib member 165 has a radially outer rim 167 and a radially inner flexible deflectable seal strip 168. The purpose of the strip 168 is to assure good sealing between the two coupling elements when they are inter-engaged. The rim 167 has a shaped surface 166, located at substantially 45° to the plane of the flange 162. Of course other angular values may be employed but about 45° is preferred. When the two coupling parts are connected together, the edges of the roof portions 130 engage the surface 166 at peripherally spaced locations. The seal strip 168 is deflected slightly radially outwardly and bears resiliently against the surface 114A of the wall 114, so providing a good seal and taking up any minor tolerance variations which may have arisen in manufacture.

In the above description, reference has been made to the surface 132 of the roof portion 130 being located in a plane substantially parallel to the planes of the surfaces 116A and 116B. It is not essential to the present invention that the surface 132 should be planar nor that it should be precisely parallel to the planar surfaces 116A and 116B. A configuration as shown in FIG. 11 may alternatively be employed, with good results.

Those skilled in the art of design of ostomy couplings will realise that certain changes and modifications may be made, without departing from the present invention. For example, the undercut formation could be positioned so as to extend radially outwardly rather than inwardly and the cooperating element would then have a radially inwardly directed rib member co-operable therewith.

I claim:

1. A method of injection moulding an undercut formation on a surface of a circular body wherein said formation is moulded in a series of arcuate sections alternating with spaces, characterised in that the moulding core which produces the formation comprises an inner core member and an outer core member, and the core is extracted by firstly relatively rotating said body and said outer core member so that the body is expanded radially by a camming action between the core and the arcuate sections and then ejecting the body off the core.

2. The method according to claim 1, characterized in that the method of moulding the undercut formation includes selecting the circular body from a closure member or a coupling member.

3. The method according to claim 1, characterised in that the arcuate sections of the undercut formation are of equal length.

4. The method according to claim 1, characterised in that the ratio of the aggregate circumferential length of the spaces to the aggregate circumferential length of the arcuate section is at least 1:3.

5. The method according to claim 1, characterised in that the spaces are of equal length.

6. The method according to claim 1, characterised in that the radial extent of the undercut formation is greater than 0.005 inch (0.0125 cm).

7. The method according to claim 1, characterised in that the ends of the respective arcuate sections are chamfered.

8. The method according to claim 1, characterised in that the circular body is held stationary and the core rotated by an amount sufficient to cause the arcuate sections to ride up out of the depressions in which they have been formed.

9. The method according to claim 1, characterised in that each of the arcuate sections has an undercut radially extending surface which subtends an angle to the axis of the circular body of at least 80°.

10. A moulded plastics closure member comprising a circular body provided with a fluid passage and an undercut formation, said formation comprising a series of arcuate sections alternating with spaces, characterised in that the ends of respective arcuate sections are chamfered and the chamfered end surfaces of the arcuate sections are located at an angle of less than 60° to a tangent to the circular body, and in that a plurality of the undercut arcuate sections each have a radially extending surface which subtends an angle to the rotational axis of the body sufficient to give a required degree of security to the closure member.

11. The moulded plastics closure member according to claim 10, characterised in that it comprises an internal wall above the undercut formation, said formation having a radial extent of greater than 0.005 inch (0.0125 cm), a plurality of the undercut arcuate sections each having a radially extending surface which subtends an angle to the rotational axis of the body of at least 80 degrees and sufficient to give a required degree of security to the closure member, the internal wall above the undercut formation being devoid of witness lines.

12. The closure member according to claim 10, characterised in that the arcuate sections of the undercut formation are of equal length.

13. The closure member according to claim 10, characterised in that the arcuate sections of the undercut formation are of unequal length.

14. The closure member according claim 10, characterised in that the ratio of the aggregate circumferential length of the spaces to the aggregate circumferential length of the arcuate sections is at least 1:3.

15. The closure member according to claim 10, characterised in that the spaces are of equal length.

16. The closure member according to claim 10, characterised in that the ends of the respective arcuate sections are chamfered and the chamfered end surfaces of the arcuate sections are located at an acute angle to a tangent to the circular body.

17. The closure assembly characterised in that it includes a closure member according to claim 10.

18. A child-resist container incorporating a closure assembly according to claim 17, characterised in that the series of arcuate sections are of unequal length which cooperate with discontinuities in a lip of the container such that, in order to open the container, the closure member needs to be rotated relative to the container until the arcuate sections are in registry with the appropriate discontinuities of the lip.

19. The coupling element for use in an ostomy, incontinence, or wound care device, the element comprising an annular body provided with an undercut formation and defining a channel for fluid communication therethrough, characterised in that said formation comprises a series of arcuate sections alternating with spaces, a plurality of the undercut arcuate sections each having a radially extending surface which subtends an angle to the axis of the body sufficient to give a required degree of security to the coupling element in respect of its attachment to a counterpart coupling element.

20. The coupling element according to claim 19, characterised in that said arcuate sections are equally angularly spaced in a peripheral sense, and each occupies an arc subtending an angle of between 25° and 15° at the axis of revolution of the coupling.

21. The coupling element according to claim 19, characterised in that there are 6, 8, 10 or 12 of said arcuate sections.

22. The coupling element according to claim 19, characterised in that the annular body comprises a channel-shaped as seen in radial section, and in which the arcuate sections extend radially inwardly from the outer wall of the channel by a distance of up to half the width of the channel.

23. The coupling element according to claim 22, characterised in that the channel has a base surface comprising a plurality of shallow recesses, serving to receive one or more mould core members.

24. The coupling element according to claim 23, characterised in that the recesses serve, in extraction of the annular body from the mould, to prevent rotation of said body relative to said mould core member.

25. The coupling for use in an ostomy, wound care or incontinence device, the coupling comprising two inter-engagable coupling elements, characterised in that one coupling element is in accordance with claim 19, and the other coupling element comprises an annular rib having thereon a flexible, resilient and deflectable seal strip arranged to co-operate with a wall of the annular channel to prevent leakage of bodily discharges.

26. The coupling according to claim 25, characterised in that the coupling element comprising the annular channel is the bag-side element and the rib is the body-side element.

27. A coupling element for use in an ostomy, incontinence, or wound care device, the element comprising an annular body provided with an undercut formation and defining a channel for fluid communication therethrough, characterised in that said formation comprises a series of arcuate sections alternating with spaces, a plurality of the undercut arcuate sections each having a radially extending surface which subtends an angle to the rotational axis of the body sufficient to give a required degree of security to the device, and the radially extending surface extending radially inwardly or outwardly, as the case may be, by a distance such that it makes a sufficient overlap with a co-operating coupling element of the device so as securely to join the two coupling elements together.

28. The coupling element according to claim 27, characterised in that the said overlap is such that the two coupling elements of the device are separable by a peeling action but not by a direct pull.

29. A coupling element of an ostomy coupling having a channel shape in cross section, having a radial inner wall defining a channel for communication of fluid therethrough and an outer wall and a floor, the element being characterised in that (i) the floor of the element has a plurality of depressions therein adjacent to the inner wall, the depressions being spaced around the channel, and (ii) the radially outer wall has a plurality of inwardly-projecting shelf-like roof portions, also spaced around the channel and extending partly across the channel from that part of the outer wall furthest from the channel floor.

* * * * *